(12) United States Patent
Bonrath et al.

(10) Patent No.: US 8,674,143 B2
(45) Date of Patent: Mar. 18, 2014

(54) SYNTHESIS OF GREEN KETONE INTERMEDIATE

(75) Inventors: Werner Bonrath, Freiburg (DE); Ulla Letinois, Saint Louis (FR); Jan Schütz, Lörrach (DE)

(73) Assignee: DSM IP Assets, B.V., Heerlen (NL)

( * ) Notice: Subject to any disclaimer, the term of this patent is extended or adjusted under 35 U.S.C. 154(b) by 0 days.

(21) Appl. No.: 13/501,805

(22) PCT Filed: Oct. 7, 2009

(86) PCT No.: PCT/EP2009/063024
§ 371 (c)(1),
(2), (4) Date: Jul. 10, 2012

(87) PCT Pub. No.: WO2010/043522
PCT Pub. Date: Apr. 22, 2010

(65) Prior Publication Data
US 2012/0283476 A1   Nov. 8, 2012

(30) Foreign Application Priority Data

Oct. 15, 2008 (EP) ................................ 08166678

(51) Int. Cl.
*C07C 45/29* (2006.01)
*C07C 35/17* (2006.01)
*C07C 49/21* (2006.01)

(52) U.S. Cl.
USPC ............................ 568/361; 568/376; 568/828

(58) Field of Classification Search
USPC ......................................... 568/361, 376, 828
See application file for complete search history.

(56) References Cited

U.S. PATENT DOCUMENTS 4,147,672 A   4/1979   Schulte-Elte et al.

FOREIGN PATENT DOCUMENTS

EP   2 128 118   12/2009

OTHER PUBLICATIONS

International Search Report for PCT/EP2009/063024, mailed Jan. 19, 2010.
Bishop et al., "A gatekeeper residue for inhibitor sensitization of protein tyrosine phosphatases", *Bioorganic & Medicinal Chemistry Letters*, vol. 16, No. 15, Aug. 1, 2006, pp. 4002-4006.

*Primary Examiner* — Sikarl Witherspoon
(74) *Attorney, Agent, or Firm* — Nixon & Vanderhye P.C.

(57) ABSTRACT

A process for the preparation of 1-ethynyl-3,3-dimethylcyclohexan-1-ol from dimedone by a reaction sequence of reduction and ethynylation and its further transformation into green ketone.

3 Claims, No Drawings

SYNTHESIS OF GREEN KETONE INTERMEDIATE

This application is the U.S. national phase of International Application No. PCT/EP2009/063024 filed 7 Oct. 2009 which designated the U.S. and claims priority to EP Patent Application No. 08166678.6 filed 15 Oct. 2008, the entire contents of each of which are hereby incorporated by reference.

The present invention relates to the synthesis of an intermediate in the synthesis of green ketone (1-(3,3-dimethylcyclohex-6-en-1-yl)-pent-4-en-1-one and/or the isomeric 1-(3,3-dimethylcyclohex-1-en-1-yl)-pent-4-en-1-one) from dimedone (5,5-dimethylcyclo-hexane-1,3-dione) and its transformation into green ketone. The intermediate is 1-ethynyl-3,3-dimethyl-1-cyclohexanol.

Green ketone is an important ingredient for the perfumery industry and can be used as perfuming and/or odor-modifying agent as well as flavoring and/or taste-modifying ingredient. Several approaches for its synthesis, e.g., from dehydro-linalool, are known (DE 25 02 767; U.S. Pat. No. 4,147,672), comprising several more or less unattractive and expensive steps like dehydration with boric acid, copper chloride catalyzed addition of allyl chloride or bromide and treatment with 80% formic acid.

On the other hand dimedone is a cheap and readily available starting material for a multi-step synthesis of green ketone. In U.S. Pat. No. 4,147,672 the reduction of dimedone in 52% yield in a two-step reaction sequence to the α,β-unsaturated mono-ketone via the monotosylhydrazone (G. A. Hiegel et al., J. Org. Chem. 38, 3637 (1973)) is described. The catalytic hydrogenation of the ketone in the presence of palladium on charcoal gave 3,3-dimethylcyclohexan-1-one (no yield given) and subsequent ethynylation with ethyne in basic medium gave 1-ethynyl-1-hydroxy-3,3-dimethylcyclohexane in about 50% yield. Reaction with CuCl and allyl chloride in basic medium gave 1-(1-hydroxy-3,3-dimethylcyclohexyl)-pent-4-en-1-yne after distillation in 50% yield. Treatment with boric acid yielded (70%) a 2:3 mixture of 1-(3,3-dimethyl-cyclohex-1-ene-1-yl)- and -6-en-1-yl)-pent-4-en-1-ine which was transformed into a 2:3 mixture of the corresponding -pent-4-en-1-ones by treatment with 80% formic acid at 90° C.

Alternatively, the α,β-unsaturated mono-ketone (3,3-dimethylcylohex-5-en-1-one) was submitted to a Wittig reaction with a solution of butyl lithium and a phosphoniumbromide salt obtained from triphenylphosphine and 5-bromopent-1-ene. Work-up gave 1-(3,3-dimethylcyclohex-5-en-1-ylidene)-pent-4-ene in 50% yield. Treatment with 40% peracetic acid in ethylene chloride gave the epoxide which was converted to green ketone in 30% yield.

It is evident that neither of the above described multi-step syntheses of green ketone starting from dimedone is technically interesting: the sluggish first reduction to the cyclohexenone; the formation of phosphorous containing waste in the Wittig reaction; the use of peracetic acid and the low overall yield.

The task was, therefore, to develop a technically interesting, economical synthesis of green ketone from dimedone which task has been solved by the present invention.

The present invention relates to a synthesis of an intermediate in the green ketone synthesis, i.e. of 1-ethynyl-3,3-dimethyl-1-cyclohexanol, from dimedone by a reaction sequence of catalytic reduction and ethinylation and to the preparation of green ketone by further submitting the 1-ethynyl-3,3-dimethyl-1-cyclohexanol to a Rupe rearrangement and transformation of the methyl-3,3-di methylcyclohexenyl-ketone into green ketone. The latter can be effected using methods well-known in the art.

The present invention also relates to the first step of the reaction sequence, i.e., to a catalytic hydrogenation of dimedone to give 3,3-dimethylcyclohexane-1-one.

The prior art with respect to this reaction is represented by J. Champagne et al., Can. J. Chem. 42, 212 (1964); Y. Sasson et al., Tetrahedron Lett. 34, 3199 (1973); B. R. Davis et al., J. Chem. Soc. Perkin Trans 1, 11, 2820 (1979); R. A. Cormier, Synth. Commun. 11, 295 (1981); and A. G. Martinez et al., Tetrahedron 43, 275 (1987).

J. Champagne et al. obtained 3,3-dimethylcyclohexan-1-one in a two-step synthesis from dimedone which was reduced with Raney-Ni in 72% yield to 3,3-dimethylcyclohexan-1-ol which again was oxidized to 3,3-dimethylcyclohexan-1-one in 95.5% yield with dichromate in sulphuric acid (overall yield 69%). The disadvantages of this route are: two steps, toxic dichromate and strong corrosive acid.

Y. Sasson et al. achieved reduction of dimedone via transfer hydrogenation in ethylene glycol as hydrogen donor in the presence of the homogenous catalyst $RuCl_2$ $(PPh_3)_3$. Among a number of different reduction products 3,3-dimethylcyclohexan-1-one was obtained only in 4% yield which is an unacceptable low selectivity.

Clemmensen reduction of dimedone with amalgamated zinc wool according to B. R. Davis et al. provided 3,3-dimethylcyclohexan-1-one in a mixture with 2,4,4-trimethylcyclopentan-1-one and 3-ethoxy-5,5-dimethylcyclohex-2-en-1-one. No yields or further work-up conditions are given. Additional disadvantage is the use of mercury and lack of details for Zn and Hg removal.

R. A. Cormier obtained 3,3-dimethylcyclohexan-1-one in 69-73% yield (98-99% purity) by Pd-catalyzed medium-pressure hydrogenation of dimedone in conc. $H_2SO_4$/propionic acid. The propionate ester of 3,3-dimethylcyclohexan-1-ol which was obtained as by-product had to be separated by distillation. The disadvantages of this method are: highly corrosive conditions which should be avoided on large scale, the formation of by-product and only moderate yield.

Finally, A. G. Martinez et al. reduced dimedone in a two-steps procedure with sodium hydride and triflic anhydride via 5,5-dimethyl-3-trifluoromethylsulfonyloxy-cyclohex-2-en-1-one which was then hydrogenated in the presence of $PtO_2$. No yields are given. The disadvantages of this procedure are the high price and corrosive nature of triflic anhydride, the expensive NaH which is used in stoichiometric amounts, the salt formation and the two steps.

Therefore, it was necessary to find reaction conditions for the reduction of dimedone to 3,3-dimethylcyclohexanone with high selectivity in one step with no or low waste formation and in the absence of strong oxidative (or corrosive) reagents and halides.

In accordance with the present invention it has been found that 3,3-dimethylcyclohexanone can be obtained from dimedone in high yield by hydrogenation with catalytic amounts of a noble metal catalyst in a polar solvent, in the presence or absence of an acid. It has surprisingly been found that the hydrogenation reaction can be carried out in the absence of an acid. Noble metals supported on a carrier are efficient catalysts for this reaction.

Among the polar solvents in which the reaction can be conducted are, without limitation, water, alcohols, ethers and alkyl esters of organic acids. Preferred are alcohols, especially $C_{1-4}$ alcohols, most preferred are methanol and isopropanol.

Noble metal catalysts for such hydrogenation are well-known and can be used, e.g., Pd, Pt, Rh, Ru, Ir. Preferably palladium catalysts are used. Among the palladium catalysts which are known and which are all useful in the present process the preferred ones are those which are commercially available, particularly on a well-known carrier such as charcoal, $Al_2O_3$, $SiO_2$, $TiO_2$, and others in well-known ratios, e.g., 5-10% w/w. A ratio of catalyst (noble metal) to dimedone of 0.005% w/w or 0.5 mole % is sufficient for very good results. Organic or inorganic acids with a pka<2 can be used, among which p-toluene sulfonic acid is preferred. Optionally the reaction can be carried out in absence of an acid. Finally, the reaction is conducted under a hydrogen pressure of 0-10 bara, preferably 1-2 bara and at temperatures of 60-110° C., preferably 75-100° C., more preferably 80-95° C.

With respect to the ethynylation step the state of the art is represented by two procedures published in U.S. Pat. No. 4,147,672 (Schulte-Elte et al.) and S. W. Pelletier et al., J. Org. Chem. 41, 1069 (1976). According to Pelletier et al. 3,3-dimethylcyclo-hexan-1-one was ethynylated by reaction with a more than stoichiometric amount of lithium acetylide-ethylenediamine in benzene/tetrahydrofuran (1:1) in 96% yield. The disadvantages are the more than stoichiometric amount of lithium alkyls required which need to be handled under strict inert conditions, which are toxic, corrosive, very reactive and generate significant amounts of waste. The same disadvantages apply if a Grignard reagent is used (ethyne/ethylmagnesium bromide) which would yield about 90% of the desired product.

On the other hand Schulte-Elte et al. have ethynylated 3,3-dimethylcyclo-hexan-1-one with ethyne in a basic medium in about 50% yield to give 1-ethynyl-3,3-dimethyl-cyclohexan-1-ol. The low yield is a disadvantage in a commercial process.

In accordance with the present invention it has been found that 1-ethynyl-3,3-dimethylcyclohexan-1-ol can be obtained in surprisingly high yields (up to 94%) while avoiding the generation of waste by reaction of 3,3-dimethylcyclohexan-1-one with ethyne in the presence of catalytic amounts of a base, preferably an alkali hydroxide in liquid ammonia using reaction conditions which are generally known for this type of reaction. The preferred conditions in the present reaction are: ethyne pressure of 10-20 bara; reaction time 30-300 minutes, more preferably 40-60 minutes; concentration of 3,3-dimethylcyclohexan-1-one in liquid ammonia 15-50% (w/w) and concentration of an aqueous base, most preferably KOH, 35-50% (w/w). Work-up is easily achieved in the usual manner.

The transformation of 1-ethynyl-3,3-dimethyl-1-cyclohexan-1-ol into green ketone can be effected in accordance with methods described in the art or in analogy with such methods. E.g., Eur. J. Org. Chem. 2, 354-365 (2004; P. Kraft et al.) describes the Rupe rearrangement of 1-ethynyl-3,3-dimethyl-1-cyclohexanol to methyl-3,3-dimethylcyclohexenyl-ketone achieved with $P_2O_5$ in toluene. This rearrangement, however, can also be achieved by the method described by V. Cadierno et al. in Adv. Synth. Catal. 348, 101-110 (2006) using an allyl-ruthenium(II) complex as a catalyst. A yield of more than 90% of isolated compound can be obtained after quantitative reaction. The reaction conditions are: refluxing in THF using 1 mmol of the propargylic alcohol in 1.0 M solution in trifluoroacetic acid.

As reported by R. W. Hasbrouck et al. in J. Org. Chem. 38, 2103-2106 (1973) α-ethynyl alcohols can be submitted to a Rupe rearrangement by refluxing the carbinols with an excess of formic acid for 2-8 hours. Best results for the ketone formation starting from 1-ethynyl-1-cyclohexanol were obtained under the following reaction conditions: 80% formic acid, 85-90° C., 8 hours: 95% conversion, 96% ketone, 1% 1-ethynylcyclohexene, 1% formylmethylene-cyclohexane. Similar good results were obtained starting from 1-ethynyl-3,3-dimethylcyclohexan-1-ol.

With respect to the last step in the synthesis of green ketone, the transformation of 1-acetyl-3,3-dimethylcyclohex-6-ene and/or 1-acetyl-3,3-dimethylcyclohex-1-ene into 1-(3,3-dimethyl-cyclohex-6-en-1-yl)- and/or 1-(3,3-dimethylcyclohex-1-en-1-yl)-pent-4-en-1-one can be achieved in accordance with methods well-known in the art or analogous thereto, e.g., by the method described in U.S. Pat. No. 4,147,672, by reaction with allyl bromide in the presence of lithium-diisopropyl-amide as basic reagent. When mixtures of isomers are used as starting materials, the final products can be separated one from the other by column chromatogra-phy on silica gel.

The following examples illustrate the invention in more detail.

EXAMPLE 1

3,3-Dimethylcyclohexan-1-one at Small Scale 312 mg of 5% Pd/C were placed in a 37 mL glass-liner. 4.38 g of dimedone (31 mmol), 7.8 g of isopropanol (10 mL) and 174 mg of p-toluene sulfonic acid (1 mmol) were added. The glass-liner was closed and stirring was started with 500 rpm. The autoclave was flushed three times with 5 bara $N_2$. The stirrer was turned off. The autoclave was pressurized with 5 bara $H_2$ for 10 minutes for pressure check. The pressure was released. The stirrer was turned on again to 500 rpm and the autoclave was heated to 85° C. internal temperature. The autoclave was pressurized with 2 bara $H_2$ and the stirrer was set to 1000 rpm. The reaction mixture was stirred under 2 bara $H_2$ at 85° C. for 2 hours and 50 minutes. Then stirring was slowed to 500 rpm, the autoclave was cooled to a temperature below 25° C. and depressurized. After three times flushing with $N_2$ at 5 bara for 100 minutes stirring was stopped and the autoclave was opened. The content was sucked and filtrated over a 0.45 μm filter. A 30 mL filtrated sample was diluted with 1 mL of isopropanol and 5 mg of $NaHCO_3$ and then analyzed by GC. The total yield of 3,3-dimethylcyclohexan-1-one was 97% with a selectivity of 97%.

EXAMPLE 2

3,3-dimethylcyclohexan-1-one at Larger Scale 41 g of 5% Pd/C E 101 N/D were placed in a 2 L glass-steel autoclave with glass-liner. 385 g of dimedone (2.75 mol), 663 g (850 mL) of isopropanol and 15.3 g (88 mmol) of p-toluene sulfonic acid were added. The glass-liner was closed and stirring was started with 500 rpm. The autoclave was flushed three times with 5 bara $N_2$. The stirrer was turned off. The autoclave was then pressurized with 5 bara $H_2$ for 10 minutes for pressure check. The pressure was released.

The stirrer was turned on again to 500 rpm and the autoclave was heated to 85° C. internal temperature. The autoclave was pressurized with 2 bara $H_2$ and the stirrer set to 1000 rpm. The reaction mixture was stirred under 2 bara $H_2$ at 85° C. for 14 hours until 123% of the theoretical $H_2$-amount had been consumed. Then stirring was slowed to 500 rpm, the autoclave was cooled to an internal temperature below 25° C. and depressurized. After three times flushing with $N_2$ at 5 bara for 100 minutes the stirring was stopped and the autoclave was opened. The content was sucked and filtrated over a 0.45 μm filter. A 30 mL filtrated sample was diluted with 1 mL of isopropanol and 5 mg of NaHCO$_3$ and then analyzed by GC. The 3,3-dimethylcyclohexan-1-one was isolated in 95% yield.

EXAMPLE 3

3,3-dimethylcyclohexan-1-one Including Isolation and Distillation 9.260 g of 5% Pd/C were placed in a 2 L glass-steel autoclave with glass-liner. 65 g of dimedone, 146 mL of isopropanol and 2.580 g of p-toluene sulfonic acid were added. The glass-liner was closed and stirring was started with 500 rpm. The autoclave was flushed three times with 5 bara N$_2$. The stirrer was turned off and the autoclave was pressurized with 5 bara H$_2$ for 10 minutes for pressure check. The pressure was released. The stirrer was turned on again to 500 rpm and the autoclave was heated to 85° C. internal temperature. The autoclave was pressurized with 2 bara H$_2$ and the stirrer was set to 1000 rpm. The reaction mixture was stirred under 2 bara H$_2$ at 85° C. until 123% of the theoretical H$_2$-amount had been consumed. Then stirring was slowed to 500 rpm, the autoclave was cooled to an internal temperature below 25° C. and depressurized. After three times flushing with N$_2$ at 5 bara for 100 minutes stirring was stopped and the autoclave was opened. The content was sucked and filtrated over a 0.45 μm filter. A 30 mL filtrated sample was diluted with 1 mL of isopropanol and 5 mg of NaHCO$_3$ and then analyzed by GC.
Work-Up:

155.95 g of the clear yellow isopropanol solution were concentrated at 40° C. and 80 mbara. The green clear residue was mixed with 210 mL of water and 140 mL of pentane. The mixture was extracted twice with 70 mL of pentane. The combined organic phases were washed with 2×140 mL of 1 N NaOH-solution and extracted twice with 140 mL of water. The last aqueous washing phase showed a pH of 6. The combined organic phases were dried over sodium sulphate and the solvent was evaporated at 40° C. bath temperature and 200 mbar. The crude product was obtained in 44.03 g (purity of 85% (GC area %)).

The crude product was purified by rectification using a column (20 cm), equipped with a vacuum jacket, packed with packing material Wilson (5 mm), and a separator, at a headtemperature of 112-114° C. at 125 mbar. The yield of the isolated product was 79.1%.

EXAMPLE 4

Hydrogenation of Dimedone in Ethyl Acetate 936 mg of 5% Pd/C were placed in a 37 mL glass-liner. 4.38 g (31 mmol) of dimedone, 7.8 g of ethyl acetate (8.6 mL) and 174 mg (1 mmol) of p-toluene sulfonic acid were added. The glass-liner was closed and stirring was started with 500 rpm. The autoclave was flushed three times with 5 bara N$_2$. The stirrer was turned off. The autoclave was pressurized with 5 bara H$_2$ for 10 minutes. The pressure was then released, the stirrer was turned on again to 500 rpm and the autoclave was heated to 85° C. internal temperature. The autoclave was pressurized with 2 bara H$_2$ and the stirrer was set to 1000 rpm. The reaction mixture was stirred under 2 bara H$_2$ at 85° C. for 5 hours and 30 minutes. Then stirring was slowed to 500 rpm and the autoclave was cooled to a temperature below 25° C. and depressurized. After three times flushing with N$_2$ at 5 bara for 100 minutes the stirring was stopped and the autoclave opened. The content was sucked and filtrated over a 0.45 μm filter. A 30 mL filtrated sample was diluted with 1 mL of isopropanol and 5 mg of NaHCO$_3$ and then analyzed by GC. The yield was 90%.

EXAMPLE 5

Hydrogenation of Dimedone in the Presence of Lactic Acid 312 mg 5% Pd/C were placed in a 37 mL glass-liner. 4.38 g (31 mmol) of dimedone, 7.8 g of (10 mL) isopropanol and 174 mg (1.9 mmol) of lactic acid were added. The glass-liner was closed and stirring was started with 500 rpm. The autoclave was flushed three times with 5 bara N$_2$. The stirrer was turned off and the autoclave was pressurized with 5 bara H$_2$ for 10 minutes. The pressure was released. The stirrer was turned on again to 500 rpm and the autoclave was heated to 85° C. internal temperature. The autoclave was pressurized with 2 bara H$_2$ and the stirrer was set to 1000 rpm. The reaction mixture was stirred under 2 bara H$_2$ at 85° C. for 5 hours and 30 minutes. Then stirring was slowed to 500 rpm and the autoclave was cooled to a temperature of below 25° C. and depressurized. After three times flushing with N$_2$ at 5 bara for 100 minutes, the stirring was stopped and the autoclave opened. The content was sucked and filtrated over a 0.45 μm filter. A 30 mL filtrated sample was diluted with 1 mL of isopropanol and 5 mg of NaHCO$_3$ and then analyzed by GC. The yield was 86%.

EXAMPLE 6

Hydrogenation of Dimedone in the Presence of a Solid Acid 312 mg 5% Pd/C were placed in a 37 mL glass-liner. 4.38 g (31 mmol) of dimedone, 7.8 g (10 mL) of isopropanol and 166 mg of Nafion NR 50 were added. The glass-liner was closed and stirring was started with 500 rpm. The autoclave was flushed three times with 5 bara N$_2$. The stirrer was turned off and the autoclave was pressurized with 5 bara H$_2$ for 10 minutes. The pressure was released. The stirrer was turned on again to 500 rpm and the autoclave was heated to 85° C. internal temperature. The autoclave was pressurized with 10 bara H$_2$ and the stirrer was set to 1000 rpm. The reaction mixture was stirred under 10 bara H$_2$ at 85° C. for 1 hours and 40 minutes. Then stirring was slowed to 500 rpm and the autoclave was cooled to a temperature below 25° C. and depressurized. After three times flushing with N$_2$ at 5 bara for 100 minutes, the stirring was stopped and the autoclave opened. The content was sucked and filtrated over a 0.45 μm filter. A 30 mL filtrated sample was diluted with 1 mL of isopropanol and 5 mg of NaHCO$_3$ and then analyzed by GC. The yield was 86%.

EXAMPLE 7

Hydrogenation of Dimedone in the Absence of an Acid 624 mg of 10% Pd/C were placed in a 37 mL glass-liner. 4.38 g (31 mmol) of dimedone and 7.8 g (10 mL) of methanol were added. The glass-liner was closed and stirring was started with 500 rpm. The autoclave was flushed three times with 5 bara N$_2$. The stirrer was turned off and the autoclave was pressurized with 5 bara H$_2$ for 10 minutes. The pressure was released. The stirrer was turned on again to 500 rpm and the autoclave was heated to 85° C. internal temperature. The autoclave was pressurized with 2 bara $H_2$ and the stirrer was set to 1000 rpm. The reaction mixture was stirred under 2 bara $H_2$ at 85° C. for 2.5 hours. Then stirring was slowed to 500 rpm and the autoclave was cooled to a temperature below 25° C. and depressurized. After three times flushing with $N_2$ at 5 bara for 100 minutes, stirring was stopped and the autoclave was opened. The content was sucked and filtrated over a 0.45 μm filter. A 30 mL filtrated sample was diluted with 1 mL of isopropanol and 5 mg of $NaHCO_3$ and then analyzed by GC. The yield was 90%.

EXAMPLE 8

Hydrogenation of Dimedone in the Absence of Acid 37.5 g of 10% Pd/C were placed in a 2 L glass-line autoclave. 350 g (2.5 mol) of dimedone and 625 g (790 mL) of methanol were added. The glass-liner was closed and stirring was started with 500 rpm. The autoclave was flushed three times with 5 bara $N_2$. The stirrer was turned off and the autoclave was pressurized with 5 bara $H_2$ for 10 minutes. The pressure was released. The stirrer was turned on again to 500 rpm and the autoclave was heated to 85° C. internal temperature. The autoclave was pressurized with 2 bara $H_2$ and the stirrer was set to 1000 rpm. The reaction mixture was stirred under 2 bara $H_2$ at 85° C. for 93 hours. Then stirring was slowed to 500 rpm and the autoclave was cooled to a temperature below 25° C. and depressurized. After three times flushing with $N_2$ at 5 bara for 100 minutes, the stirring was stopped and the autoclave opened. The content was sucked and filtrated over a 0.45 μm filter. A 30 mL filtrated sample was diluted with 1 mL of isopropanol and 5 mg of $NaHCO_3$ and then analyzed by GC. The yield was 94%.

EXAMPLE 9

1-Ethynyl-3,3-dimethylcyclohexan-1-ol

In a 2 L autoclave, 370 g of ammonia were added to 100.0 g (96.7%, 766.1 mmol) of 3,3-dimethylcyclohexan-1-one and 880.8 mg (15.7 mmol) of aqueous KOH (40.14% (w/w)) at 288 K. Ethyne was added under stirring (1200 rpm, 11.0 bara). The reaction started with the addition of ethyne. During the reaction ethyne was added semi-continuously in order to adjust the reaction pressure at 11.0 bara with the aid of a pressure control valve. After 40 minutes at 15° C. the reaction was stopped. For work-up the ammonia was evaporated and 200 g of hexane were added to the reaction mixture. The mixture was acidified with acetic acid (pH 7.0), the light yellow solution was dried over anhydrous sodium sulphate, and the hexane was evaporated at 10 mbar/40° C. A brown liquid was obtained and analyzed by GC. Yield of 1-ethynyl-3,3-dimethylcyclohexan-1-ol: 93.8%; conversion: 94.7%; selectivity: 99.0%; purity 93.4%.

EXAMPLE 10

In analogy to the method of Example 9, starting from 200.0 g (96.7%, 1532.2 mmol) of 3,3-dimethylcyclohexan-1-one and 1767.2 mg (31.5 mmol) of KOH, after 75 minutes 240.99 g of 1-ethynyl-3,3-dimethylcyclohexan-1-ol were obtained. Yield of 1-ethynyl-3,3-dimethylcyclohexan-1-01: 90.8%; conversion: 92.0%; selectivity: 98.7%; purity 89.6%.

EXAMPLE 11

In analogy to the method of Example 9, starting from 240.0 g (99.9%, 1899.1 mmol) of 3,3-dimethylcyclohexan-1-one and 2120.6 mg (37.8 mmol) of KOH, after 120 minutes 292.24 g of 1-ethynyl-3,3-dimethylcyclohexan-1-ol were obtained. Yield of 1-ethynyl-3,3-dimethylcyclohexan-1-01: 86.0%; conversion: 87.5%; selectivity: 98.3%; purity 85.1%.

EXAMPLE 12

In analogy to the method of Example 9, starting from 280.5 g (99.0%, 2199.2 mmol) of 3,3-dimethylcyclohexano-1-ne and 2474.0 mg (44.1 mmol) of KOH, after 180 minutes 335.12 g of 1-ethynyl-3,3-dimethylcyclohexan-1-ol were obtained. Yield of 1-ethynyl-3,3-dimethylcyclohexan-1-01: 87.6%; conversion: 91.6%; selectivity: 95.7%, purity 87.6%.

The invention claimed is:
1. A method of preparing 1-ethynyl-3,3-dimethylcyclohexan-1-ol comprising
  (a) reducing dimedone (5,5-dimethylcyclo-hexane-1,3-dione) to 3,3-dimethycyclo-hexan-1-one by hydrogenation with catalytic amounts of a noble metal catalyst in a polar solvent and optionally in the presence of an acid to produce 3,3-dimethylcyclohexane-1-one, and
  (b) ethynylating the 3,3-dimethylcyclohexanone with ethyne in the presence of catalytic amounts of a base in liquid ammonia
to produce 1-ethynyl-3,3-dimethyl-1-cyclohexanol.
2. The process of claim 1, wherein in step (a) the dimedone is hydrogenated in a polar solvent in the presence of catalytic amounts of an acid and a noble metal catalyst.
3. A process for the preparation of green ketone, wherein the 1-ethynyl-3,3-dimethylcyclohexan-1-ol prepared according to the method of claim 1 is subjected to a Rupe rearrangement and the methyl-3,3-dimethyl-cyclohexenyl-ketone obtained is transformed into green ketone.

* * * * *

UNITED STATES PATENT AND TRADEMARK OFFICE
CERTIFICATE OF CORRECTION

PATENT NO. : 8,674,143 B2  Page 1 of 1
APPLICATION NO. : 13/501805
DATED : March 18, 2014
INVENTOR(S) : Bonrath et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 419 days.

Signed and Sealed this
Twenty-ninth Day of September, 2015

Michelle K. Lee
*Director of the United States Patent and Trademark Office*